(12) United States Patent
Masson (10) Patent No.: US 11,172,938 B2
(45) Date of Patent: Nov. 16, 2021

(54) DYNAMIC LOCKING DEVICE (71) Applicant: Medtronic Xomed, Inc., Jacksonville, FL (US)

(72) Inventor: Martin Masson, Keller, TX (US)

(73) Assignee: Medtronic Xomed, Inc., Jacksonville, FL (US)

( * ) Notice: Subject to any disclaimer, the term of this patent is extended or adjusted under 35 U.S.C. 154(b) by 118 days.

(21) Appl. No.: 16/298,138

(22) Filed: Mar. 11, 2019

(65) Prior Publication Data
US 2019/0201006 A1  Jul. 4, 2019

Related U.S. Application Data (63) Continuation of application No. 15/383,817, filed on Dec. 19, 2016, now Pat. No. 10,226,260, which is a continuation of application No. 13/870,675, filed on Apr. 25, 2013, now Pat. No. 9,526,509.

(51) Int. Cl.
*A61B 17/16* (2006.01)
*B23B 31/14* (2006.01)

(52) U.S. Cl.
CPC ........ *A61B 17/162* (2013.01); *A61B 17/1615* (2013.01); *A61B 17/1617* (2013.01); *A61B 17/1622* (2013.01); *A61B 17/1624* (2013.01); *B23B 31/14* (2013.01)

(58) Field of Classification Search
CPC ............ A61B 17/1615; A61B 17/1617; A61B 17/162; A61B 17/1622
See application file for complete search history.

(56) References Cited

U.S. PATENT DOCUMENTS

| | | | |
|---|---|---|---|
| 2,901,258 A | * | 8/1959 | Brandafi ............... B23B 31/113 279/97 |
| 2,983,519 A | | 5/1961 | Staunt |
| 3,495,844 A | | 2/1970 | Dee |
| 3,556,540 A | | 1/1971 | Benjamin et al. |
| 3,590,232 A | | 6/1971 | Sadowski |
| 3,672,256 A | | 6/1972 | Kosmowski |
| 4,006,996 A | | 2/1977 | Kasabian |
| 4,436,512 A | | 3/1984 | Garcia |

(Continued)

FOREIGN PATENT DOCUMENTS

| | | |
|---|---|---|
| EP | 2988679 A1 | 3/2016 |
| JP | UMAS5760611 | 9/1955 |

(Continued)

OTHER PUBLICATIONS

Canadian Office Action dated Apr. 24, 2020 in corresponding Canadian Application No. 2,909,354.

(Continued)

*Primary Examiner* — Anu Ramana
(74) *Attorney, Agent, or Firm* — Harness, Dickey & Pierce, P.L.C.

(57) ABSTRACT

A surgical instrument including a tool, a handpiece, and a locking member. The handpiece includes both a coupling member configured to cooperate with the tool, and a driver for rotating the tool. The locking member is movable from an unlocked position to a locked position in response to centrifugal force generated during rotation of the locking member. The locking member is configured to secure the tool to the handpiece when in the locked position.

13 Claims, 4 Drawing Sheets

(56) References Cited

U.S. PATENT DOCUMENTS

| | | | |
|---|---|---|---|
| 5,735,535 | A | 4/1998 | McCombs et al. |
| 5,833,246 | A | 11/1998 | Trott |
| 5,833,704 | A | 11/1998 | McCombs et al. |
| 5,921,563 | A | 7/1999 | Huggins et al. |
| 6,045,564 | A | 4/2000 | Walen |
| 7,011,661 | B2 | 3/2006 | Riedel et al. |
| 8,137,362 | B2 | 3/2012 | Malinowski |
| 9,364,295 | B2 | 6/2016 | Bossier |
| 9,526,509 | B2 | 12/2016 | Masson |
| 10,226,260 | B2 | 3/2019 | Masson |
| 2003/0009177 | A1 | 1/2003 | Middleman et al. |
| 2003/0023256 | A1 | 1/2003 | Estes et al. |
| 2005/0181329 | A1 | 8/2005 | Maitre |
| 2007/0243499 | A1 | 10/2007 | Bowen |
| 2008/0193236 | A1 | 8/2008 | Durfee |
| 2012/0244495 | A1 | 9/2012 | Bossler |
| 2012/0259337 | A1 | 10/2012 | del Rio et al. |
| 2017/0095260 | A1 | 4/2017 | Masson |

FOREIGN PATENT DOCUMENTS

| | | |
|---|---|---|
| JP | S55135455 U | 9/1980 |
| JP | H04-505429 A | 9/1992 |
| JP | 2009505683 A | 2/2009 |
| JP | 4713042 B2 | 6/2011 |
| JP | 2012-071128 A | 4/2012 |
| JP | 5760611 B2 | 8/2015 |
| WO | 2012-138338 A1 | 10/2012 |
| WO | 2014176060 A1 | 10/2014 |

OTHER PUBLICATIONS

Australian Office Action dated Dec. 3, 2018 in corresponding/related Australian Application No. 2014257380.

Communication pursuant to Rules 161(1) and 162 EPC dated Dec. 3, 2015 for European Application No. 147232813 corresponding to PCT/US2014/033977 claiming benefit of U.S. Appl. No. 13/870,675, filed Apr. 25, 2013.

European Office Action dated Mar. 23, 2017 for EP Application No. 14723281.3 corresponding to PCT/US2014/033977 claiming benefit of U.S. Appl. No. 13/870,675, filed Apr. 25, 2013.

International Preliminary Report on Patentability dated Nov. 5, 2015 for PCT/US2014/033977 claiming benefit of U.S. Appl. No. 13/870,675, filed Apr. 25, 2013.

International Search Report and Written Opinion dated Aug. 8, 2014 for PCT/US2014/033977 claiming benefit of U.S. Appl. No. 13/870,675, filed Apr. 25, 2013.

Japanese Office Action dated Aug. 15, 2017 for JP Application No. 2016-510696 corresponding to PCT/US2014/033977 claiming benefit of U.S. Appl. No. 13/870,675, filed Apr. 25, 2013.

Japanese Office Action dated Dec. 2, 2016 for JP Application No. 2016-510696 corresponding to PCT/US2014/033977 claiming benefit of U.S. Appl. No. 13/870,675, filed Apr. 25, 2013.

Japanese Office Action dated Mar. 1, 2019 in corresponding Japanese Application No. 2018-089734.

U.S. Appl. No. 13/870,675, U.S. Pat. No. 9,526,509, filed Apr. 25, 2013, Masson.

U.S. Appl. No. 15/383,817, U.S. Pat. No. 10,226,260, filed Dec. 19, 2016, Masson.

European Office Action dated Oct. 2, 2019 for EP Application No. 14723281.3.

Japanese Office Action (with Enlglish translation) for corresponding Application No. 2018089734 dated Nov. 29, 2019.

Office Action dated Nov. 30, 2020, in corresponding Canadian Application No. 2,909,354.

Japanese Office Action (with English translation) regarding Japanese Application No. 2020-134493, dated Jun. 18, 2021.

* cited by examiner

DYNAMIC LOCKING DEVICE

CROSS-REFERENCE TO RELATED APPLICATIONS

This application is a continuation of U.S. patent application Ser. No. 15/383,817 filed on Dec. 19, 2016, which is a continuation of U.S. patent application Ser. No. 13/870,675 filed on Apr. 25, 2013, now U.S. Pat. No. 9,526,509 issued on Dec. 27, 2016. The entire disclosure of the above application is incorporated herein by reference.

FIELD

The present disclosure relates to a dynamic locking device. For example, the present disclosure relates to a dynamic locking device for coupling a tool, such as a drill bit, to a handpiece for rotating the tool.

BACKGROUND

This section provides background information related to the present disclosure which is not necessarily prior art.

High-speed surgical instruments facilitate a surgeon's work during surgery. Such instruments often include a handpiece with a motor therein for rotating a tool coupled to the handpiece. A variety of different tools can be individually coupled to the handpiece, such as a drill bit. Typically, two or more steps are required to couple a tool to a handpiece, such as: (1) inserting and pushing the tool into an attachment or collet of the handpiece; and (2) turning the tool or attachment/collet of the handpiece to a locked position. To release the tool, at least two steps are again required, such as: (1) turning the tool or attachment/collet of the handpiece to an unlocked position; and (2) pulling the tool out from within the handpiece. The turning step can be cumbersome and demand attention of the surgeon or operator that could be better devoted elsewhere during surgery. A high-speed handpiece and tool that can be coupled together without the need for turning the tool or a portion of the handpiece would therefore be desirable.

SUMMARY

This section provides a general summary of the disclosure, and is not a comprehensive disclosure of its full scope or all of its features.

The present teachings provide for a surgical instrument including a tool, a handpiece, and a locking member. The handpiece includes both a coupling member configured to cooperate with the tool, and a driver for rotating the tool. The locking member is movable from an unlocked position to a locked position in response to centrifugal force generated during rotation of the locking member. The locking member is configured to secure the tool to the handpiece when in the locked position.

The present teachings further provide for a surgical instrument assembly including a tool, a locking member coupled to the tool, and a handpiece. The locking member includes a first flexible tab. The handpiece includes a coupling member configured to receive the tool and the locking member therein. The coupling member is connected to a driver for rotating the tool. Upon rotation of the tool by the driver, the first flexible tab flexes outward from a longitudinal axis of the locking member from a retracted position to an expanded position to lock the tool to the handpiece.

The present teachings also provide for a surgical instrument assembly including a tool and a locking member. The locking member is coupled to the tool and includes first and second flexible expansion tabs. The first and second flexible expansion tabs are a first distance from a longitudinal axis of the locking member when the locking member and the tool are stationary. The first and second flexible expansion tabs flex outward to a second distance from the longitudinal axis of the locking member when the locking member and the tool are rotating, the second distance is greater than the first distance. At the second distance the first and second flexible tabs are configured to abut a first internal flange of a handpiece configured to rotate the tool thereby locking the tool to the handpiece.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figures 1, 2:
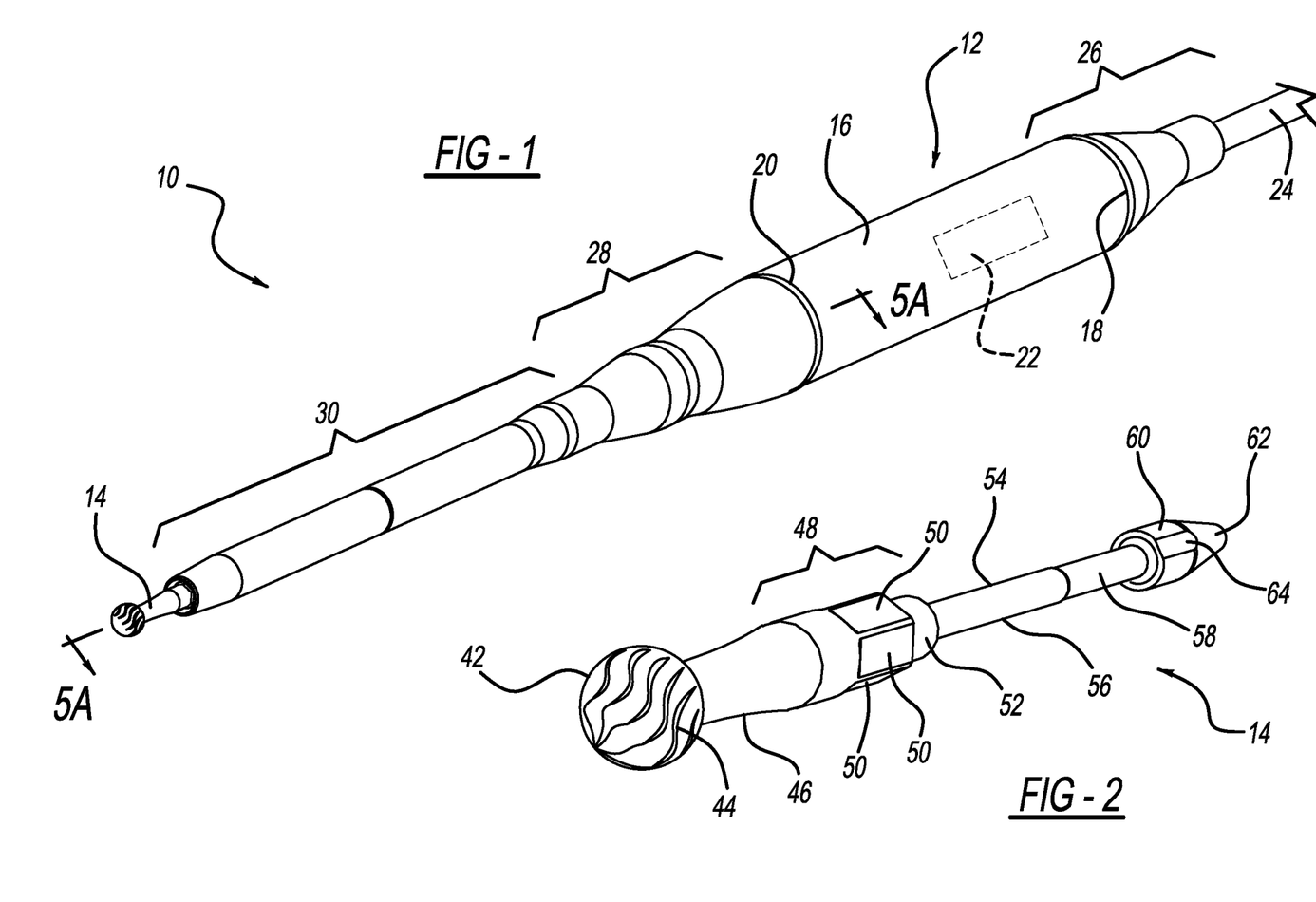
FIG. 1 is a perspective view of a high-speed handpiece and a tool coupled thereto.
FIG. 2 is perspective view of the tool of FIG. 1 decoupled from the handpiece.

With initial reference to FIG. 1, a surgical instrument assembly according to the present teachings is illustrated at reference numeral 10. The surgical instrument assembly 10 generally includes a handpiece 12 and a tool 14. The tool 14 can be removeably coupled to the handpiece 12 merely by linearly sliding the tool 14 into the handpiece 12. To decouple the tool 14 from the handpiece 12, the tool 14 need only be pulled out from within the handpiece 12. Advantageously and as described in detail herein, the present teachings eliminate a turning step whereby the tool 14 or a portion of the handpiece 12 is turned in order to couple and decouple the tool 14. In particular, the present teachings eliminate the need for a collet, for example.

The handpiece 12 generally includes a main body 16 with a first end 18 and a second end 20, which is opposite to the first end. The first end 18 is generally a proximal end and the second end 20 is generally a distal end. The main body 16 houses a motor 22, which rotates the tool 14 at a desired speed and in a desired direction. The motor 22 can be any suitable motor, such as an electric motor or a pneumatic motor. A cord or hose 24 extends from the main body 16. When the motor 22 is an electric motor, the cord 24 extends from the main body 16 to a power source to deliver power to the motor 22 for driving the motor 22. When the motor 22 is a pneumatic motor, the hose 24 includes a high pressure gas inlet (for air, nitrogen, or other types of pressurized gas) and a gas outlet.

At the first end 18 of the main body 16 is a first conical interface member 26. The first conical interface member 26 is tapered inward toward the cord 24, which extends through the first conical interface member 26. A diameter of the first conical interface member 26 is greatest at the first end 18 of the main body 16, and is smallest at a point of the first conical interface member 26 furthest from the first end 18.

At the second end 20 of the main body 16 is a second conical interface member 28. The second conical interface member 28 tapers inward as it extends away from the second end 20 of the main body 16. Coupled to and extending from the second conical interface member 28 is a housing assembly 30, which houses a portion of the tool 14 and a drive shaft for driving the tool 14, as described herein.

With reference to FIG. 2, the tool 14 is illustrated in greater detail. The tool 14 can be any suitable tool for use during a surgical procedure, such as a drill bit as illustrated. Any suitable drill bit for drilling or cutting tissue or bone can be used. As illustrated, the tool 14 includes a drill bit tip 42. The drill bit tip 42 is generally spherical and includes cutting flutes 44. The cutting flutes 44 can be any suitable cutting member defined by, or coupled to, the drill bit tip 42, such as curved and sharpened recesses within the drill bit tip 42. Extending from the drill bit tip 42 is a neck 46, which connects the drill bit tip 42 to a coupling body 48 of the tool 14. The coupling body 48 includes coupling surfaces 50, which can be any suitable coupling surfaces to couple the tool 14 to a rotating member of the handpiece 12 to transfer torque from the handpiece 12 to the tool 14, as described herein. For example and as illustrated, the coupling surfaces 50 include a plurality of planar and spaced apart surfaces configured to mate with corresponding surfaces of the handpiece 12. Any suitable number of the coupling surfaces 50 can be provided, such as 6 to provide a hexagonal arrangement of the coupling surfaces 50.

The coupling body 48 further includes a reduced diameter portion 52. The reduced diameter portion 52 is on a side of the coupling surfaces 50 opposite to the neck 46 and the drill bit tip 42. The reduced diameter portion 52 has a smaller diameter than the remainder of the coupling body 48, such as an area of the coupling body 48 including the coupling surfaces 50.

Extending from the coupling body 48, and particularly from the reduced diameter portion 52, is a stem 54 of the tool 14. The stem 54 includes a first diameter portion 56 and a second diameter portion 58. The first diameter portion 56 is between the coupling body 48 and the second diameter portion 58. The first diameter portion 56 has a larger diameter than the second diameter portion 58.

Mounted to the stem 54, is a base 60 of the tool 14. The stem 54 is thus between the coupling body 48 and the base 60. A conical end 62 extends from a side of the base 60 that is opposite to the stem 54. The base 60 includes one or more planar surfaces 64 at an outer periphery thereof. The planar portions 64 allow air to escape from within distal cavity 146 of coupling member 130 when the base 60 is inserted in the distal cavity 146, as described herein and illustrated in FIGS. 5B and 5C for example.

Figure 3A:
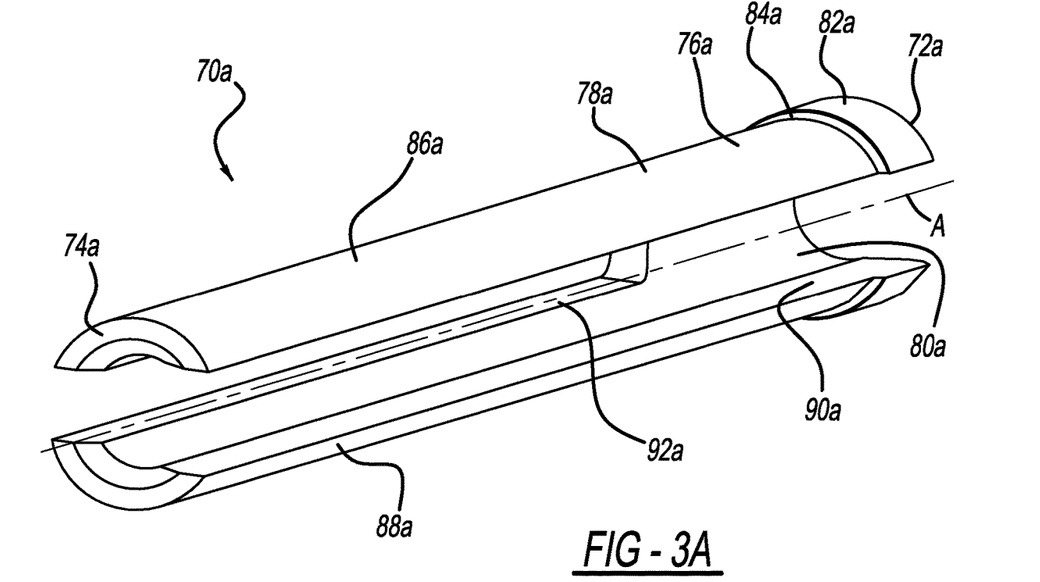
FIG. 3A is a perspective view of a locking device according to the present teachings for locking the tool to the hand-piece.

With additional reference to FIG. 3A, a locking number 70a of the tool 14 is illustrated. The locking member 70a generally includes a first end or proximal end 72a, which is opposite to a second end or distal end 74a. The locking member 70a includes a base 76a at the first end 72a. An outer surface 78a of the base 76a is opposite to an inner surface 80a of the base 76a. The base 76a further includes a retention member 82a at the first end 72a. The retention member 82a extends outward and away from a longitudinal axis A of the locking member 70a to provide the base 76a with an enlarged outer diameter at the first end 72a. The retention member 82a defines a flange 84a at the outer surface 78a of the base 76a.

The locking member 70a further includes a first flexible expansion tab 86a and a second flexible expansion tab 88a. Both the first and the second flexible expansion tabs 86a and 88a extend from the base 76a to the second end 74a. The first and second flexible expansion tabs 86a and 88a are spaced apart to define a first slot 90a and a second slot 92a therebetween. The first slot 90a extends entirely between the first end 72a and the second end 74a, and thus the first slot 90a is partially defined by the base 76a. The second slot 92a extends from the base 76a to the second end 74a. The locking member 70a can be made of any suitable material, such as a flexible material. Any suitable flexible material can be used, such as a suitable polymer.

Although the locking member 70a includes a first flexible expansion tab 86a and a second flexible expansion tab 88a, any suitable number of flexible expansion tabs can be included, such as only a single flexible expansion tab (only the first flexible expansion tab 86a or only the second flexible expansion tab 88a, for example). For example and with reference to FIG. 3B, locking member 70b can include a third flexible expansion tab 94b in addition to first and second flexible expansion tabs 86b and 88b. The third flexible expansion tab 94b extends from the base 76b to the second end 74b of the locking member 70b. The second slot 92b is defined between the first flexible expansion tab 86b and the third flexible expansion tab 94b. A third slot 96b is defined between the third flexible expansion tab 94b and the second flexible expansion tab 88a. But for the third flexible expansion tab 94b and the third slot 96b, the locking member 70b is substantially similar to the locking member 70a and thus like features are illustrated with the same reference numbers, but include the letter "b" rather than the letter "a."

Figure 3B:
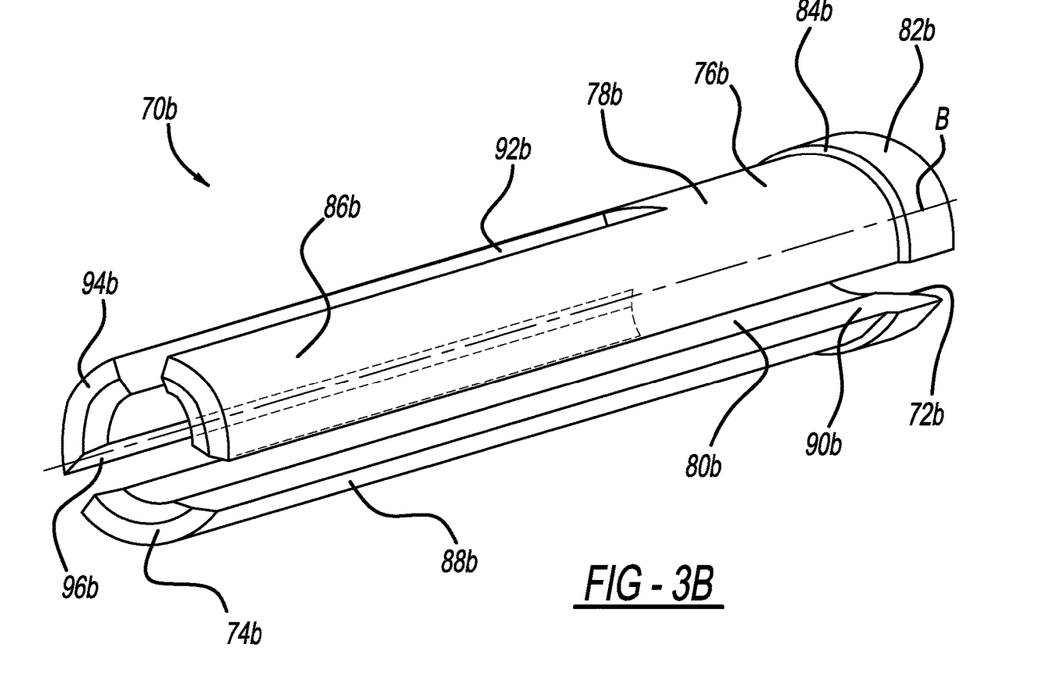
FIG. 3B is a perspective view of another locking device according to the present teachings for locking the tool to the hand-piece.

The locking member 70a or the locking member 70b, for example, is coupled to the tool 14 at the stem 54. Coupling of the locking member 70a to the stem 54 will now be described. The locking member 70b is coupled to the stem 54 in substantially the same manner.

Figure 5A:
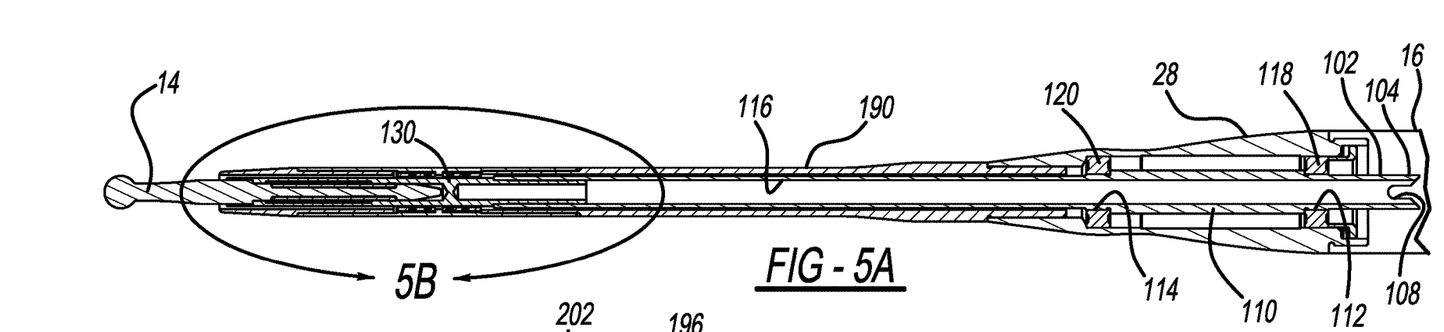
FIG. 5A is a cross-sectional view taken along line 5A-5A of FIG. 1.
Figure 5B:
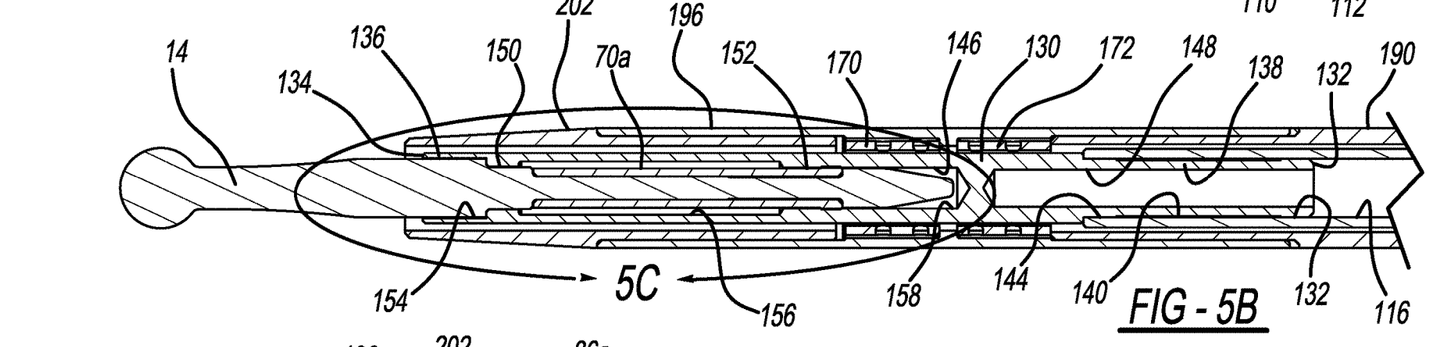
FIG. 5B is cross-sectional view of area 5B of FIG. 5A.
Figure 5C:
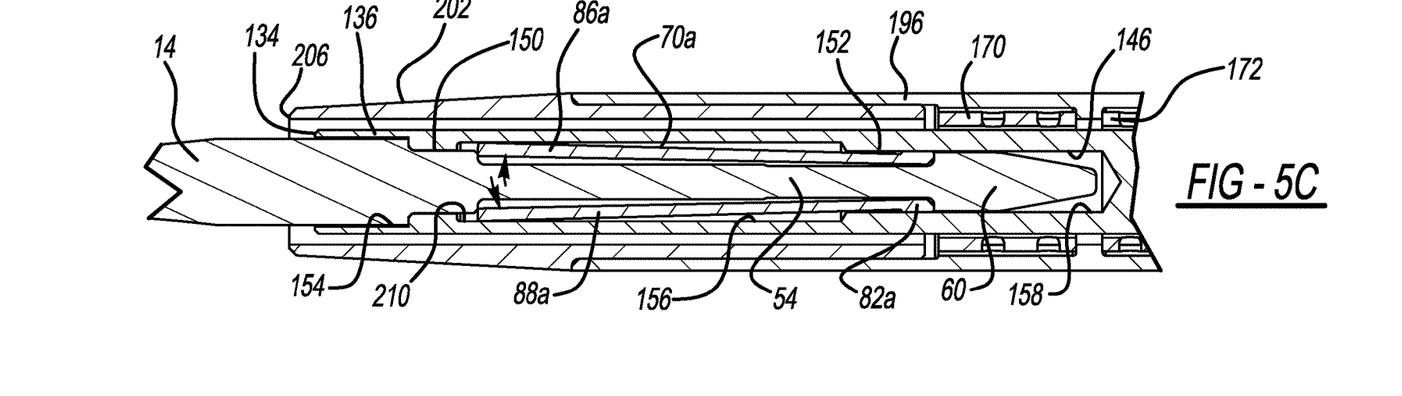
FIG. 5C is a cross-sectional view of area 5C of FIG. 5B.

The locking member 70a can be clipped on to the stem 54 by pressing the locking member 70a onto the stem 54 such that the stem 54 passes through the first slot 90a and is seated against the inner surface 80a of the base 76a. For example, the locking member 70a can be positioned alongside the tool 14 and pressure can be applied to the side of the locking member 70a opposite to the side defining the first slot 90a. The pressure causes the first and second flexible expansion tabs 86a and 88a to expand to permit the stem 54 to pass through the first slot 90a. The locking member 70a then clamps onto the stem 54 such that the locking member 70a rotates with the stem 54 when the tool 14 rotates. The base 76a is positioned at the second diameter portion 58 of the stem 54. The first end 72a of the locking member 70a is positioned at or against the base 60. The locking member 70a extends along the stem 54 toward the coupling body 48, such that the second end 74*a* is proximate to the reduced diameter portion 52 of the coupling body 48, as illustrated in FIGS. 5A-5C.

The first and second flexible expansion tabs 86*a* and 88*a* are arranged and made of a material such that upon rotation of the tool 14 with the locking member 70*a* coupled thereto and rotating therewith, the first flexible expansion tab 86*a* and the second flexible expansion tab 88*a* will flex radially outward from the longitudinal axis A. Similarly, when the locking member 70*b* is coupled to the tool 14 in the same manner and at the same position described above with respect to the locking member 70*a*, the first, second, and third flexible expansion tabs 86*b*, 88*b*, and 94*b* will flex radially outward from the longitudinal axis B of the locking member 70*b*. As explained herein, the first and second flexible expansion tabs 86*a* and 88*a* as well as the first, second, and third flexible expansion tabs 86*b*, 88*b*, and 94*b* flex radially outward in response to centrifugal force, thereby causing them to expand outward and retain the tool 14 coupled to the handpiece 12.

Figure 4:
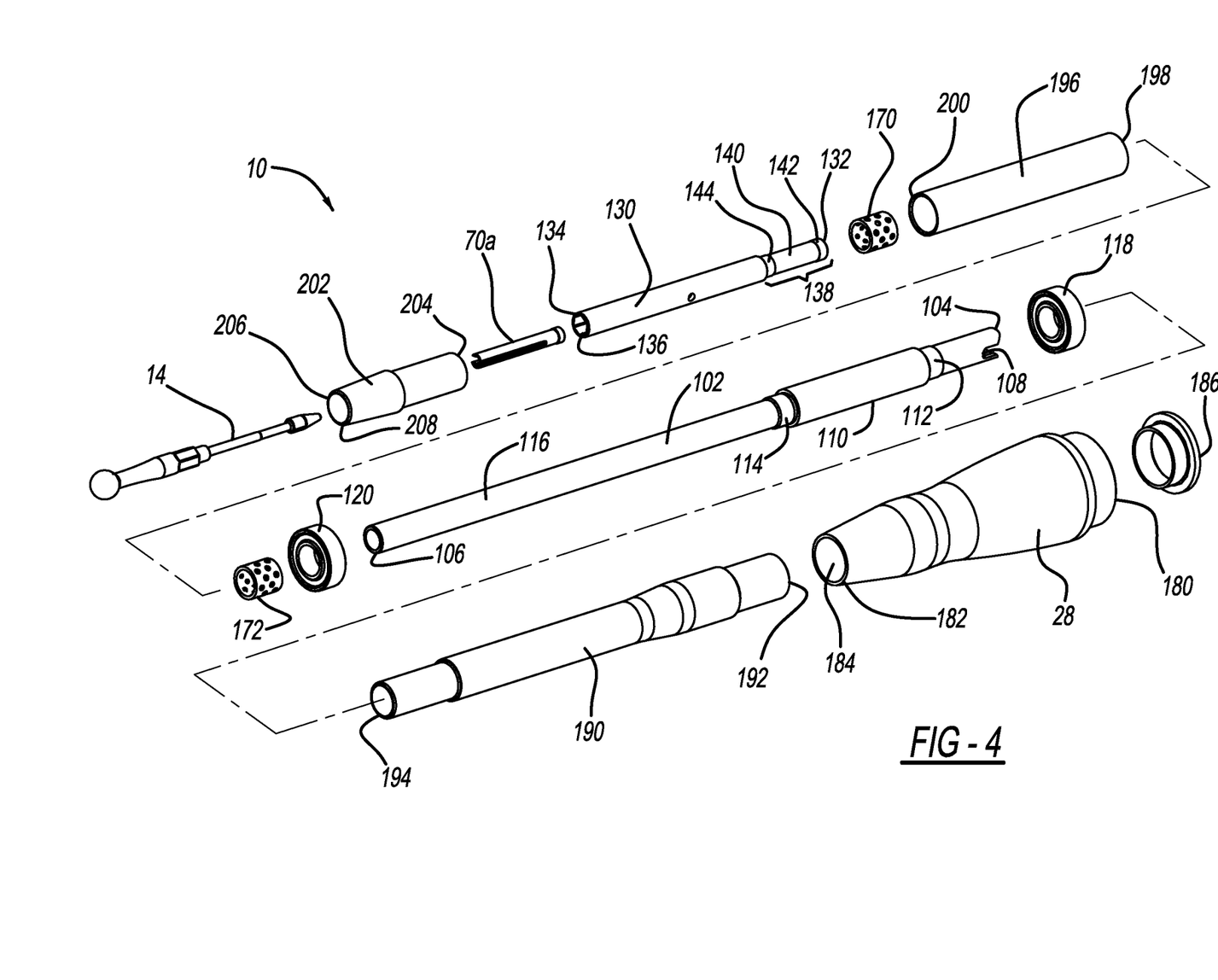
FIG. 4 is an exploded view of the handpiece of FIG. 1.

With reference to FIG. 4, the surgical instrument assembly 10 further includes a driver 102. The driver 102 includes a proximal end 104 and a distal end 106, which is opposite to the proximal end 104. At the proximal end 104 is an interface 108, which is illustrated as a generally u-shaped interface defined by the driver 102 at the proximal end 104 thereof. The interface 108 can be any suitable interface or coupling device, feature, or member configured to couple the driver 102 to an output of the motor 22 to transfer rotational torque generated by the motor 22 to the driver 102 in order to rotate the driver 102.

Near the proximal end 104 is an enlarged diameter portion 110 of the driver 102. At a proximal end of the enlarged diameter portion 110 is a proximal shoulder 112. At a distal end of the enlarged diameter portion 110 is a distal shoulder 114. Extending from the distal shoulder 114 is an elongated drive shaft 116. The elongated drive shaft 116 extends from the distal shoulder 114 to the distal end 106 of the driver 102. The enlarged diameter portion 110 includes an outer diameter that is greater than an outer diameter of the drive shaft 116. The proximal shoulder 112 and the distal shoulder 114 each have an outer diameter that is greater than the outer diameter of the drive shaft 116, and less than the outer diameter of the enlarged diameter portion 110.

A proximal driver bearing 118 is seated on the proximal shoulder 112. A distal driver bearing 120 is seated on the distal shoulder 114. The position of the proximal and distal driver bearings 118 and 120 is illustrated in FIG. 5A, for example. The proximal and distal driver bearings 118 and 120 facilitate rotation of the driver 102 within the second conical interface member 28 and the housing assembly 30 as further described herein.

With continued reference to FIG. 4, the surgical instrument assembly 10 further includes a coupling member 130. The coupling member 130 includes a proximal end 132 and a distal end 134 opposite thereto. The coupling member 130 includes an inner coupling surface 136 proximate to the distal end 134. The inner coupling surface 136 can be configured in any suitable manner in order to mate with the coupling surfaces 50 of the tool 14 in order to transfer torque from the coupling member 130 (generated by the motor 22 and transferred to the coupling member 130 by the driver 102) to the tool 14. For example and as illustrated, the inner coupling surface 136 can include a plurality of planar surfaces sized, shaped, and arranged to mate with each one of the coupling surfaces 50 of the tool 14. Therefore, when six coupling surfaces 50 are included, the inner coupling surface 136 can include six planar surfaces each one of which is configured mate with a different one of the coupling surfaces 50.

The coupling member 130 further includes a reduced diameter portion 138 at the proximal end 132 and extending therefrom. The reduced diameter portion 138 includes an intermediate part 140, a proximal part 142 at the proximal end 132, and a distal part 144. The intermediate part 140 is between the proximal part 142 and the distal part 144. The proximal part 142 and the distal part 144 have similarly sized outer diameters, each of which are greater than an outer diameter of the intermediate part 140. The reduced diameter portion 138 has an overall outer diameter that is less than a remainder of the coupling member 130 between the reduced diameter portion 138 and the distal end 134.

With additional reference to FIG. 5B, the coupling member 130 defines a distal cavity 146 and a proximal cavity 148 therein. The distal cavity 146 extends proximally from the distal end 134 of the coupling member 130. The proximal cavity 148 extends distally from the proximal end 132. The distal cavity 146 and the proximal cavity 148 are spaced apart at an interior of the coupling member 130 and thus, as illustrated, do not meet. The distal cavity 146 and the proximal cavity 148 can be configured as a single cavity extending between the proximal end 132 and the distal end 134, however. The proximal cavity 148 reduces the weight of the coupling member 130, and allows the coupling member 130 to be provided at a reduced weight. The proximal cavity 148 need not be included, however, and thus the coupling member 130 may be solid at the region of the proximal cavity 148

The distal cavity 146 includes a distal internal flange 150 and a proximal internal flange 152. The distal internal flange 150 is between the distal end 134 of the coupling member 130 and the proximal internal flange 152. The distal internal flange 150 and the proximal internal flange 152 can be annular flanges extending continuously about an internal diameter of the coupling member 130, or can each include a plurality of flange portions located at various intervals. The coupling member 130 includes a distal internal diameter 154, an intermediate internal diameter 156, and a proximal internal diameter 158. The distal internal diameter 154 is between the distal internal flange 150 and the distal end 134 of the coupling member 130. The intermediate internal diameter 156 is between the distal internal flange 150 and the proximal internal flange 152. The proximal internal diameter 158 is on a side of the proximal internal flange 152 opposite to the intermediate internal diameter 156. The intermediate internal diameter 156 is greater than the proximal internal diameter 158, and smaller than the distal internal diameter 154. The distal internal diameter 154 is greater than each of the intermediate internal diameter 156 and the proximal internal diameter 158.

To facilitate rotation of the coupling member 130 as further described herein, the housing assembly 30 further includes a distal coupling member bearing 170 and a proximal coupling member bearing 172. The bearings 170 and 172 can be any suitable type of bearing configured and sized to fit over the coupling member 130, as illustrated in FIGS. 5A-5C, for example. The bearings 170 and 172 are positioned such that an inner surface thereof abuts, or closely abuts, an outer diameter of the coupling member 130, and an outer surface of the bearings 170 and 172 abuts an inner surface of the housing assembly 30, as further described herein.

With continued reference to FIG. 4, both the second conical interface member 28 at the second end of the main body 16, as well as the housing assembly 30 will now be described in further detail. The second conical interface member 28 includes a proximal end 180 and a distal end 182. The second conical interface member 28 is cannulated and includes a distal aperture 184 at the distal end 182. It is the proximal end 180 that is coupled to the second end 20 of the main body 16. For example, the proximal end 180 can be inserted within the main body 16 at the second end 20 thereof and secured to the second end 20 in any suitable manner, such as with a suitable mechanical coupling, such as a threaded connection or quick-connect coupling for example, to facilitate coupling of various second conical interface members 28 of different lengths. A cap 186 is coupled to the second conical interface member 28, as illustrated in FIG. 5A. The cap 186 transfers force exacted by a spring (not shown), such as a wave spring, to an outer race of the proximal bearing 118 to "pre-load" the proximal bearing 118. The pre-load ensures that balls of the bearing 118 are always in contact with both inner and outer races of the bearing 118 to reduce or eliminate play. This reduces bearing wear and prolongs the life of the bearing 118. The spring can be located between the cap 186 and the motor 22.

Coupled to the second conical interface member 28 at the distal end 182 thereof is a proximal drive shaft housing 190. The proximal drive shaft housing 190 includes a proximal end 192 and a distal end 194 opposite thereto. The proximal drive shaft housing 190 is cannulated between the proximal end 192 and the distal end 194. At the proximal end 192, the proximal drive shaft housing 190 has a diameter sized to permit receipt of the proximal end 192 within the distal end 182 of the second conical interface member 28 in order to couple the proximal drive shaft housing 190 thereto. The proximal drive shaft housing 190 and the second conical interface member 28 can be secured together in any suitable manner, such as with a press-fit, a suitable adhesive, or with a mechanical coupling, such as a threaded connection for example.

The housing assembly 30 further includes a distal drive shaft housing 196. The distal drive shaft housing 196 includes a proximal end 198 and a distal end 200. The distal drive shaft housing 196 is cannulated between the proximal end 198 and the distal end 200. The proximal end 198 is sized and shaped to couple with the distal end 194 of the proximal drive shaft housing 190. For example, and as illustrated, the proximal end 198 is sized and shaped to receive the distal end 194 therein. The distal drive shaft housing 196 and the proximal drive shaft housing 190 can be coupled together in any suitable manner, such as with a press-fit, a suitable adhesive, or with a mechanical coupling, such as a threaded connection for example.

The housing assembly 30 further includes a tool housing 202. The tool housing 202 includes a proximal end 204 and a distal end 206. The tool housing 202 is cannulated between the proximal end 204 and the distal end 206, and defines a distal aperture 208 at the distal end 206. The proximal end 204 is sized and shaped to be received within the distal end 200 of the distal drive shaft housing 196. The proximal end 204 of the tool housing 202 can be secured within the distal end 200 of the distal drive shaft housing 196 in any suitable manner, such as with a press-fit, an adhesive, or with a mechanical coupling, such as a threaded connection for example.

With reference to FIGS. 5A and 5B, the driver 102 extends from the main body 16 of the handpiece 12, where the proximal end 104 of the driver 102 is coupled to the motor 22 for rotation by the motor 22. The driver 102 is supported within the second conical interface member 28 with ball bearings 118 and 120 respectively seated on the proximal shoulder 112 and the distal shoulder 114 of the driver 102. The drive shaft 116 extends beyond the distal end 182 of the second conical interface member 28, and through the proximal drive shaft housing 190 to nearly the distal end 194 thereof. Within the proximal drive shaft housing 190 proximate to the distal end 194, the drive shaft 116 is coupled to the coupling member 130 at the reduced diameter portion 138 thereof. The coupling member 130 extends from within the proximal drive shaft housing 190, through the distal drive shaft housing 196, and to the tool housing 202.

The proximal internal diameter 158 of the coupling member 130 is sized and shaped to receive portions of the tool 14 therein. Specifically and with reference to FIG. 5C for example, with the locking member 70a (or the locking member 70b) seated on the stem 54 of the tool 14 as described above, the tool 14 is inserted within the distal cavity 146 of the coupling member 130 such that the base 60 and the conical end 62 are at the proximal internal diameter 158.

The retention member 82a passes beyond the proximal internal flange 152 of the coupling member 130 as the retention member 82a is moved to the proximal internal diameter 158. Cooperation between the retention member 82a and the proximal internal flange 152 retains the tool 40 within the distal cavity 146 of the coupling member 130, such as when the coupling member 130 is stationary. To remove the tool 14 from within the coupling member 130 when stationary, only enough force need be applied to pull the retention member 82a back over the proximal internal flange 152.

The distal internal flange 150 of the coupling member 130 sits on the reduced diameter portion 52 of the coupling body 48 of the tool 14 in order to help align the inner coupling surface 136 of the coupling member 130 with the coupling surfaces 50 of the tool 14 to facilitate engagement therebetween. As a result, torque of the coupling member 130 is transferred to the tool 14 at the coupling body 48, and specifically between the inner coupling surface 136 and the coupling surfaces 50.

With reference to FIG. 5C, rotation of the driver 102 by the motor 22 results in rotation of the coupling member 130 and the tool 14 due to the couplings therebetween described above. As the tool 14 rotates, centrifugal force causes the first and second flexible expansion tabs 86a and 88a to radially expand outward from the longitudinal axis A of the locking member 70a, and move towards and potentially in contact with the inner surface of the coupling member 130 at the intermediate internal diameter 156 of the distal cavity 146 to move the first and second flexible expansion tabs 86a and 88a from a retracted position (FIG. 5B) to an expanded position (FIG. 5C).

When in the expanded position of FIG. 5C, the first and second flexible expansion tabs 86a and 88a lock the tool 14 within the coupling member 130. Specifically, the tool 14 cannot be removed from within the distal cavity 146 of the coupling member 130 because in the expanded orientation of FIG. 5C, the first and second flexible expansion tabs 86a and 88a will contact the distal internal flange 150 at a proximal end 210 to prevent removal. Therefore, when the tool 14 is rotating it will not be possible for the tool 14 to be decoupled and move out from within the coupling member 130.

Once the tool 14 is returned to the stationary position, the first and second flexible expansion tabs 86a and 88a will return to the retracted position of FIG. 5B, thereby permitting the tool 14 to be axially removed from within the coupling member 130 and from the handpiece 12 in general without having to manually rotate the tool 14 or any portion of the handpiece 12. For example, there is no need to lock and unlock the tool 14 to the handpiece 12 with a collet. The tool 14, or any other suitable tool, can thus be only linearly inserted into the coupling member 130 and locked therein merely upon use of the tool 14 to cause rotation thereof sufficient to cause the first and second flexible expansion tabs 86a and 88a to move to the expanded and "locked" position of FIG. 5C. The locking member 70a thus allows the tool 14 to be easily locked and unlocked to the handpiece 12 with only a simple axial movement of the tool 14 relative to the handpiece 12, and replaced with another tool 14, for example, without requiring the additional steps of rotating either the tool 14 or a portion of the handpiece 12, such as a collet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for locking a surgical tool to a handpiece, comprising:
   attaching the surgical tool to a separate locking member before inserting the surgical tool into the handpiece;
   only linearly inserting the surgical tool and the separate locking member into the handpiece to couple the surgical tool and locking member to the handpiece;
   locking the surgical tool to the handpiece by rotating the surgical tool and the separate locking member in the handpiece; and
   wherein attaching the surgical tool to the separate locking member includes resiliently receiving the surgical tool into a resilient slot defined in the locking member and extending along an entire length of the locking member.

2. The method of claim 1, further comprising unlocking the surgical tool from the handpiece by ceasing rotation of the surgical tool with the handpiece.

3. The method of claim 2, further comprising linearly removing the surgical tool from the handpiece upon ceasing rotation of the surgical tool with the handpiece.

4. The method of claim 1, wherein attaching the surgical tool to the locking member includes pressing the separate locking member onto a stem of the surgical tool.

5. The method of claim 4, wherein pressing the separate locking member onto the stem of the surgical tool further includes passing the stem into the resilient slot of the locking member.

6. The method of claim 1, wherein locking the surgical tool to the handpiece further includes engaging a resilient portion of the separate locking member to a flange within the handpiece upon rotating both the surgical tool and the separate locking member.

7. The method of claim 1, wherein only linearly inserting both the surgical tool and the separate locking member into the handpiece further includes linearly inserting both the surgical tool and the locking member into a rotatable coupling member positioned within the handpiece.

8. The method of claim 1, wherein locking the surgical tool to the handpiece further includes rotating the surgical tool and the separate locking member so that at least one flexible tab of the locking member radially expands by way of centrifugal force to lock the surgical tool into the handpiece.

9. A method for locking a surgical tool to a handpiece, comprising:
   attaching a surgical tool to a separate locking member;
   with the surgical tool attached to the separate locking member linearly inserting both the surgical tool and the locking member into the handpiece; and
   locking the surgical tool to the handpiece by only linearly inserting both the surgical tool and the locking member into the handpiece and rotating the surgical tool and locking member with the handpiece to cause a portion of the locking member to flex to prevent removal of the surgical tool and locking member from the handpiece.

10. The method of claim 9, further comprising unlocking the surgical tool and the locking member from the handpiece by ceasing rotation of the surgical tool and the locking member with the handpiece.

11. The method of claim 10, further comprising linearly removing the surgical tool and the locking member from the handpiece upon ceasing rotation of the surgical tool and the locking member with the handpiece.

12. The method of claim 9, wherein attaching the locking member to the surgical tool further includes clipping the locking member onto a stem of the surgical tool by expanding a slot defined in the locking member to open as the stem passes through the slot and clamps onto the stem.

13. The method of claim 9, wherein attaching the surgical tool to the locking member includes resiliently receiving the surgical tool into a resilient slot defined in the locking member, wherein the resilient slot extends an entire length of the locking member.

* * * * *

UNITED STATES PATENT AND TRADEMARK OFFICE
CERTIFICATE OF CORRECTION

PATENT NO. : 11,172,938 B2
APPLICATION NO. : 16/298138
DATED : November 16, 2021
INVENTOR(S) : Martin Masson It is certified that error appears in the above-identified patent and that said Letters Patent is hereby corrected as shown below:

On the Title Page

Column 2, Item (56) U.S. Patent Documents, Line 9, after "Garcia", insert --¶5,147,165 9/1992 Tempest 5,634,933 6/1997 McCombs et al.--

In the Specification

Column 4, Line 1, delete "number" and insert --member-- therefor

Column 6, Line 31, after "148", insert --.--

Column 8, Line 25, delete "40" and insert --14-- therefor

Signed and Sealed this
Seventeenth Day of May, 2022

Katherine Kelly Vidal
*Director of the United States Patent and Trademark Office*